United States Patent [19]

Cadet et al.

[11] Patent Number: 5,392,635
[45] Date of Patent: Feb. 28, 1995

[54] ACOUSTIC ANALYSIS OF GAS MIXTURES

[75] Inventors: Gardy Cadet, Orange; Jorge L. Valdes, Bedminster, both of N.J.

[73] Assignee: AT&T Corp., Murray Hill, N.J.

[21] Appl. No.: 175,828

[22] Filed: Dec. 30, 1993

[51] Int. Cl.$^6$ ............................................. G01N 29/02
[52] U.S. Cl. ...................................... 73/24.01; 73/597
[58] Field of Search .................... 73/24.01, 597, 61.49, 73/61.79, 64.53, 61.75

[56] References Cited

U.S. PATENT DOCUMENTS

| | | | |
|---|---|---|---|
| 2,568,277 | 9/1951 | Eltgroth | 73/24.01 |
| 4,004,461 | 1/1977 | Lynnworth | 73/194 |
| 4,011,473 | 3/1977 | Massa | 310/8.2 |
| 4,520,654 | 6/1985 | Terhune | 73/24 |
| 4,576,047 | 3/1986 | Lauer et al. | 73/597 |
| 4,596,133 | 6/1986 | Smalling et al. | 73/24 |
| 4,662,212 | 5/1987 | Noguchi et al. | 73/24.01 |
| 5,060,506 | 10/1991 | Douglas | 73/24.01 |
| 5,115,670 | 5/1992 | Shen | 73/61.41 |
| 5,247,826 | 9/1993 | Frola et al. | 73/24.01 |

FOREIGN PATENT DOCUMENTS

| | | |
|---|---|---|
| WO92/03724 | 3/1992 | Australia . |
| WO87/06703 | 11/1987 | Finland . |
| 2456510 | 8/1976 | Germany ............................ 73/24.01 |
| 3009566 | 9/1981 | Germany ............................ 73/24.01 |
| 10157 | 1/1991 | Japan .................................. 73/24.01 |
| 798323 | 7/1958 | United Kingdom ............... 73/24.01 |
| 2215049A | 9/1989 | United Kingdom . |

OTHER PUBLICATIONS

MacChesney, J. B. et al., "A New Technique for the Preparation of Low–Loss and Graded–Index Optical Fibers," *Proc. IEEE*, vol. 62, 1974, pp. 1280–1281.

*Primary Examiner*—Thomas P. Noland
*Assistant Examiner*—Joseph W. Roskos
*Attorney, Agent, or Firm*—Margaret A. Burke

[57] ABSTRACT

The present invention provides an acoustic cell for determining the composition of gas mixtures. The acoustic gas composition analysis cell has transducers acoustically isolated from the cell body through the use of an acoustic isolation material positioned at least between the transducers and the transducer housings to produce a signal-to-noise ratio of at least 4 to 1. Additionally, the transducers employed in the acoustic cell operate in the kilohertz range, reducing attenuation in the gas mixture being analyzed. The cell body employs vacuum seals which permit the use of the cell in line with vacuum equipment.

8 Claims, 3 Drawing Sheets

ACOUSTIC ANALYSIS OF GAS MIXTURES

BACKGROUND OF THE INVENTION

1. Field of the Invention

The invention relates to the field of acoustic gas monitoring and, more particularly, to the in-line monitoring and control of the composition of gas mixtures.

2. Description of the Related Art

In many manufacturing operations, accurate information concerning a reaction gas composition is necessary to control a particular process. For example, chemical vapor deposition (CVD) processes require precise gas mixtures to reliably create materials of a specific composition. Formation of semiconductor materials and optical fiber preforms often involves incorporation of dopant materials in very small concentrations. The dopant material is supplied by a dopant precursor gas which is mixed with other deposition gases in a reaction chamber. Because of the low concentration used in the vapor deposition process, the dopant gas is usually mixed with a carrier gas to ensure an even distribution of dopant within the reaction chamber. The carrier gas must deliver a consistent quantity of the dopant gas. In-line gas monitoring is often used to ensure this consistent deliver.

Acoustic monitoring of gases can employ ultrasound, i.e., sound waves having a frequency ranging from a few kHz to 10 MHz. Acoustic techniques have been extensively used for gas flow monitoring. More recently, efforts have turned to developing acoustic cells and processes which can determine the concentration of a component of a binary gas mixture. In general, acoustic concentration analysis of a gas mixture is performed by measuring the speed with which sound waves propagate through a gas mixture. Because the speed at which the sound waves travel through a gas is related to molecular weight, the concentration of a component of a gas mixture can be accurately detained.

For a single component system under ideal conditions, the velocity of sound, $V_s$ can be obtained from the following equation:

$$V_S = \left(\frac{\gamma RT}{M}\right)^{\frac{1}{2}}$$

where $\gamma$ is the specific heat capacity ratio ($C_p/C_v$), R is the universal gas constant (8.3143 J/mol K), T is the absolute temperature in Kelvins, and M is the molecular weight of the gas in kg.

In the case of a binary gas mixture, a similar relationship exists, with $\gamma$ and M replaced by $\overline{\gamma}$ and $\overline{M}$. The acoustic velocity of a binary gas mixture is then represented by:

$$V_S = \left(\frac{\overline{\gamma} RT}{\overline{M}}\right)^{\frac{1}{2}}$$

where $\overline{\gamma}$ is the average specific heat capacity ratio given by:

$$\overline{\gamma} = 1 + \left[\frac{x}{(\gamma_2 - 1)} + \frac{1-x}{(\gamma_1 - 1)}\right]^{-1}$$

and $\overline{M}$ is the mean molecular weight of the binary gas mixture given by:

$$M = (1-x)M_1 + xM_2$$

where x is the mole fraction of a second gas and $M_1$ and $M_2$ are the respective molecular weights of the first and second gases.

To solve for the concentration of a gas component, x, a quadratic equation is formulated from the above equations:

$$x^2 + \left\{\frac{[A + V_S^2(c - 2d)](a - 1) + [V_S^2 d - A](b - 1)}{V_S^2[(c - d)(b - 1) + (d - c)(a - 1)]}\right\}x +$$

$$\frac{(a - 1)(V_S^2 d - Ab)}{V_S^2[(c - d)(b - 1) + (d - c)(a - 1)]} = 0$$

Where:
- A = constant = RT
- a ≡ $\gamma_2$ and b ≡ $\gamma_1$,
- c ≡ $M_2$ and d ≡ $M_1$.
- x = concentration (mole fraction) of species corresponding to parameters a and c
- (1 − x) concentration (mole fraction) of species corresponding to parameters b and d
- $V_s$ is in units of meter/second.

This equation is solved for x using the quadratic formula. Thus, the measurement of the velocity of sound through a binary gas mixture yields the relative amounts of the two gas components.

The principle of acoustic gas analysis has been used in a gas monitoring cell shown in published UK Patent Application GB 2,215,049, the disclosure of which is incorporated by reference herein. In the disclosed cell, ultrasonic pulses are generated by an ultrasonic transducer. The transducer is composed of a piezoelectric material, such as lead zirconate titanate, and is positioned opposite a second transducer. The transit time of sonic pulses between the transducers is measured and used to yield the sound velocity. From the velocity, the composition of the binary mixture is determined.

In the cell of the U.K. patent application, metal gaskets are employed for gas sealing. Because these metal gaskets permit acoustic coupling through the body of the cell, each transducer is supported on an array of mounting pins to minimize acoustic coupling between the transducer and the cell body.

Although the cell of the U.K. application reduces acoustic coupling, there is still sufficient extraneous noise to interfere with the acoustic measurement process. The result is a loss of sensitivity of the cell. Additionally, the cell of the U.K. application operates using ultrasonic frequencies on the order of one megahertz. In general, as sound frequency increases, the attenuation of sound waves also increases. At frequencies in the megahertz range, attenuation of sound in the gas being analyzed is a problem, particularly when attempting to measure high sound absorptive gases, which absorb ultrasound in higher ultrasonic frequency ranges. Because the cell of the U.K. application has a short path length, higher frequencies are required to attain the resolution needed to detect the arriving pulse.

In U.S. Pat. No. 5,060,506, a method and apparatus are disclosed for monitoring the ratio of gases in a two-gas mixture using ultrasound. The transmitter used to generate the ultrasonic pulses is excited with a signal having a plurality of successive bursts, each of which includes a preselected number of excitation pulses at the resonant frequency. The initial pulse in each burst is separated from the final pulse in the preceding burst by a quiescent time period of sufficient duration to assure dissipation of transients so that standing waves do not form.

There is a need in the art for improved acoustic cells and methods for analyzing the composition of gas mixtures. More particularly, there is a need in the art for acoustic cells which are compatible with vacuum environments without acoustic coupling of the transducer to the cell body. Additionally, there is a need in the art for an acoustic gas composition analysis cell which operates in a frequency range which permits measurement of a wide variety of gas mixtures.

Summary of the Invention

The present invention solves both the problems of unwanted acoustic coupling and vacuum compatibility by providing an acoustic gas composition analysis cell having transducers acoustically isolated from the cell body to produce a signal-to-noise ratio of at least 4:1. The transducers employed in the acoustic cell operate in the kilohertz range, reducing attenuation in the gas mixture being analyzed. The cell body employs vacuum seals which permit the use of the cell in line with vacuum equipment.

DETAILED DESCRIPTION

Figure 1:
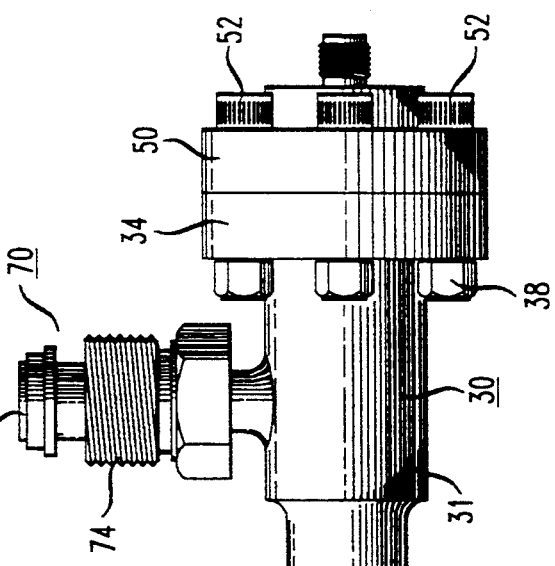
FIG. 1 is a side view of an acoustic gas analysis cell according to the present invention.
Figure 1:
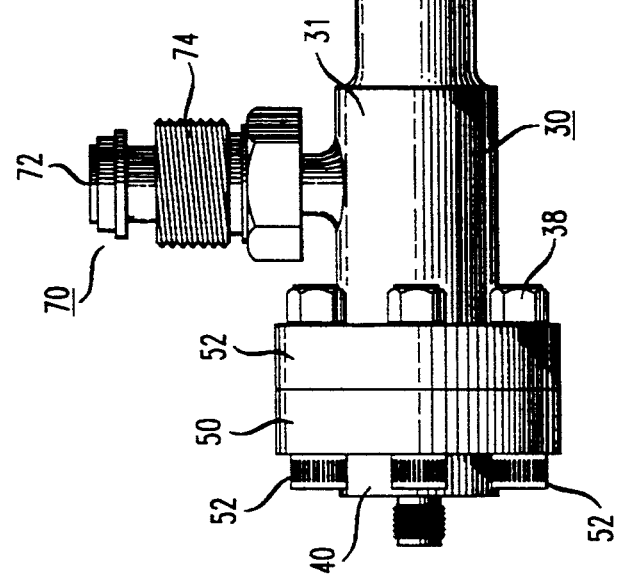

Turning now to the drawings in detail in which like reference numerals identify like or similar elements in each of the several views, FIG. 1 illustrates an exemplary acoustic gas composition analysis cell according to the present invention. The acoustic gas composition analysis cell 10 includes an electropolished stainless steel cylindrical conduit 20 for propagating sound waves through a gas mixture to be analyzed. 316 stainless steel is an exemplary stainless steel for fabricating conduit 20. First and second transducer housings 40 are coupled adjacent each end of conduit 20 by flange members 30.

Figure 2:
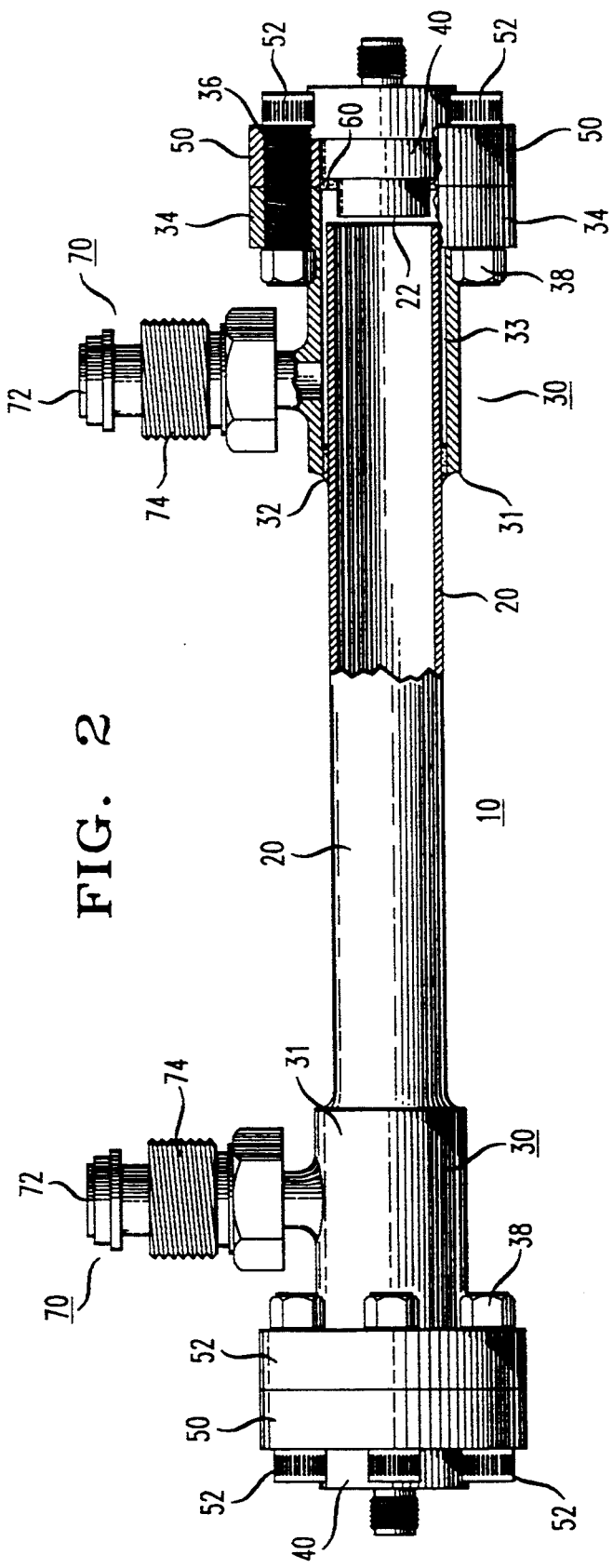
FIG. 2 is a side view in partial cross section of the acoustic gas analysis cell of FIG. 1 illustrating the relationship of the transducer housing to the gas conduit.
Figure 3:
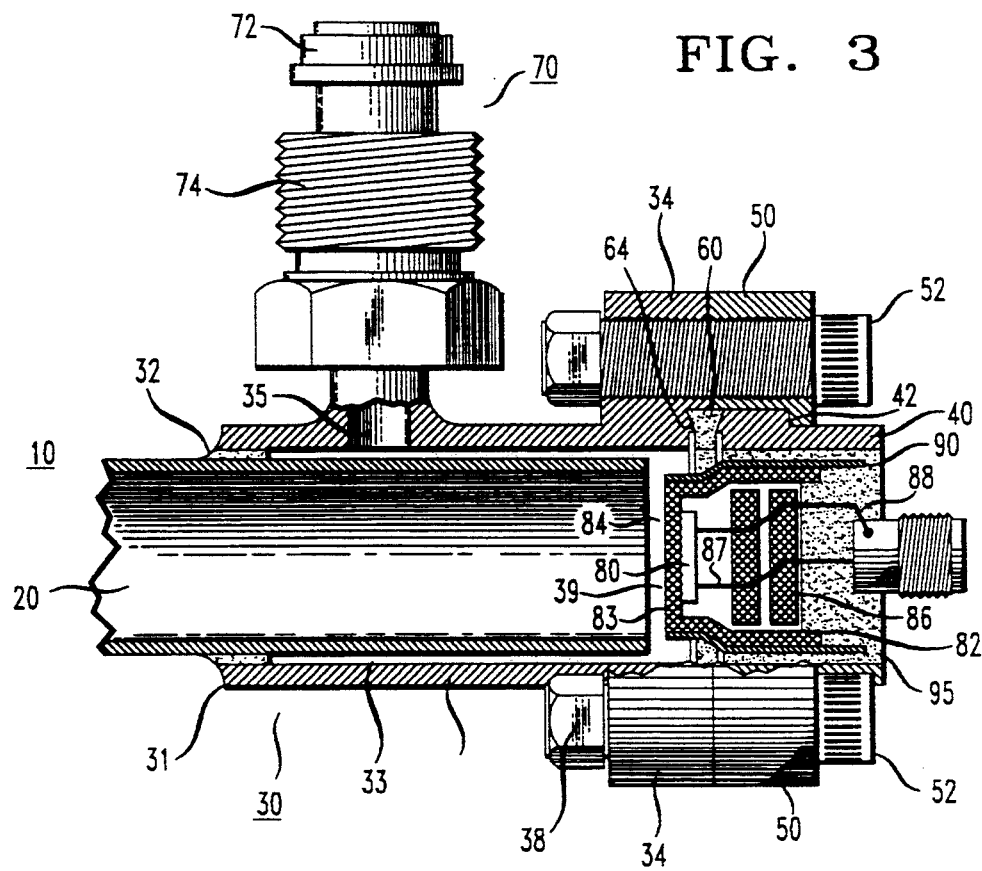
FIG. 3 is an enlarged side view in partial cross-section of a transducer and housing assembled in the acoustic gas analysis cell of the present invention, illustrating gas flow into the cell.

As best seen in FIGS. 2 and 3, flange members 30 each include a hollow cylindrical portion 31 which coaxially surrounds conduit ends 22 to define ring-like spaces 33. At one end, flange member cylindrical portion 31 is affixed to conduit 20 through weld 32. At its other end, flange member cylindrical portion 31 terminates in flange rim 34. The flange rim 34 is provided with a plurality of through-holes 36 for receiving threaded fasteners from a mating flange.

Mating flange 50 is an annular disk which engages transducer housing 40 at housing lip 42 to position the transducer housing adjacent conduit end 22. Flange 50 includes through-holes 56 which align with through-holes 36 of flange rim 34 to receive threaded fasteners 52. Threaded fasteners 52 extend through both sets of through-holes 36 and 56 and are engaged by receiving nuts 38.

Transducer housings 40 must be engaged with flange members 30 in an airtight manner to ensure compatibility of the gas analysis cell with a vacuum system. For this reason, gaskets 60 are made from a metal such as copper and are positioned between flanges 40 and 50. Gaskets 60 include knife edges 64, best seen in FIG. 3, ensuring a leak-free seal which resists degradation from noxious gases and can withstand vacuum evacuation in the ultrahigh vacuum range. When assembled, transducer housings 40 position transducers 80 adjacent conduit ends 22 to define cylindrical gaps 39. Cylindrical gaps 39 are in fluid communication with the ring-like space 33 between conduit 20 and flange member 30. The use of a separable transducer housing 40 facilitates replacement of the transducer in the event of a transducer failure or the desire to use a transducer having a different resonant frequency.

To enable gas mixtures to flow through the acoustic cell, apertures 35 are provided through the wall of flange member cylindrical portion 31. Gas ports 70 are welded to the flange member wall, enabling fluid communication with space 33 and cylindrical gap 39, best seen in FIG. 3. Each gas port 70 includes a mating member 72 such as a male VCR TM gland engaged within a threaded fastener 74 for facilitating connection to a gas line. In use, one gas port serves as the gas inlet while the other port serves as a gas outlet. As gas flows into a gas port, it passes into ring-like space 33 and cylindrical gap 39 as illustrated by the arrows in FIG. 3. The gas then flows into the conduit 20 through open conduit ends 22. At the opposite end of the cell, the pathway is reversed, and gas exits through the remaining gas port. Advantageously, this gas pathway configuration promotes uniform flow distribution around the transducer, minimizing the dead volume and improving the dynamic response of the device.

The transducer 80 is selected from piezoelectric materials, such as lead-zirconate-titanate crystals. The transducer thickness is chosen to achieve a desired resonant frequency, e.g., a resonant frequency in the kilohertz range, while acoustic isolation layer 82 and impedance matching thicknesses are comparable to the selected transducer layer thickness. Lead zirconate titanate transducers having resonant frequencies in the range of 50 to 300 kilohertz and, more particularly, 200–215 kilohertz are examples of transducers which can be used in the acoustic cells of the present invention. These frequency ranges are high enough to accurately measure acoustic signal time-of-flight in low molecular weight gases, but not so high as to incur absorption loss in the gas being measured. Both transducers are acoustically matched, i.e., they operate at the same frequency and impedance, thus increasing the signal collected at the receiving transducer. The transducers operate at the resonant frequency which produces the highest output per unit input of electrical signal.

To accurately measure the transit time of sound waves within conduit 20, transducers 80 must be acoustically isolated from the transducer housing and other acoustic cell components. Acoustic isolation helps ensure that sound is propagated through the gaseous mixture rather than through the various components of the acoustic cell housing. To this end, sleeves 90, coaxially received within transducer housings 40, are provided to house transducers 80 and their affiliated components. Within each sleeve 90, transducer 80 is coupled to a layer of acoustic isolation material 82. Acoustic isolation material 82 can be an elastomeric material such as a silicone elastomer. Material 82 attenuates radial sound from the resonating transducer and also assists in preventing extraneous noise from being transmitted through the housings and into the gas mixture being analyzed.

Because the acoustic impedance of a gas is substantially less than the acoustic impedance of the transducer, an impedance matching material 83 is optionally positioned between transducers 80 and the gas mixture to be analyzed. The term "impedance matching" is used to denote a material having an acoustic impedance which is intermediate that of the gas and the transducer. Impedance matching material 83 can be an elastomeric material such as a silicone, and can be formed separate from acoustic isolation material 82 or can be integrally formed with acoustic isolation material 82 as shown. Advantageously, use of an impedance matching material increases the acoustic power at the vibrating surface which can be coupled into the gas to be analyzed by reducing reflection of longitudinal sound waves. Increased power permits sound measurements well above the noise level in the system, i.e., to produce a system with a high signal-to-noise ratio. A signal-to-noise ratio of 4:1 is sufficiently high to obtain adequate time-of-flight measurement, with signal-to-noise ratios of greater than 10:1 being exemplary.

For applications where exposure to the gas mixture would degrade impedance matching material, a thin layer 84 of inert metal, such as gold, can be deposited over the impedance matching material. Layer 84 can be deposited by vapor deposition or sputtering. The thickness of layer 84 is selected to be effectively transparent to transmission of sound waves by the transducer while protecting the underlying material. Thicknesses of 1–2 microns have been found to have these characteristics.

To effectively absorb acoustic energy radiating from the back surface, space 85 and backing material 86 are positioned behind transducer 80. Spacing 85 is selected to be $\frac{1}{4}$ wavelength of the operating frequency of the transducer to improve acoustic attenuation. Materials such as foams and other sponge-like materials are examples of backing material 86. Optionally the backing material is supported by a sound reflecting wall to reflect sound into the backing material, useful for very short time-of-flight acoustic signals. Depending upon the desired acoustic impedance of the region behind transducer 80, the entire area may be filled with a backing material or an air gap. The backing material 86 and space 85 also effectively attenuate extraneous noise transmitted through the transducer housing 40 and sleeve 90 by the remaining cell components, improving the signal to noise ratio. Additionally, the backing material minimizes "ringing" of the transducer, i.e., the undesirable radial vibrations due to even resonances.

Sleeve 90, coupled to acoustic isolation material 82 and transducer 80, is assembled with backing material 86 to transducer housing 40 through the use of a fixing agent 95. The fixing agent serves both to mount the components in their proper position within transducer housing 40 and hermetically seal the unit for use with vacuum systems. Additionally, the fixing agent electrically isolates the transducer leads from the cell body. For this reason, the fixing agent can be an epoxy resin selected for compatibility with vacuum systems, such as TORR SEAL®, available from Varian Corporation, Lexington, Mass. The fixing agent 95 assists in attenuating extraneous noise, further promoting acoustic isolation of the transducers as well as performing its vacuum sealing function.

Transducer leads 87 and 88 pass through backing material 86 and fixing agent 95 to connect the transducers to a signal generating and data processing circuit. Typically, leads 87 and 88 are molybdenum wires formed sufficiently thin so that the effective impedance is much less than that of the transducer crystal to achieve a mismatch loss of energy that would otherwise travel through the leads. In general, the acoustic cell of the present invention may be connected to a variety of signal generators/data processors. The basic characteristics of such systems are that they stimulate a transmitting transducer to generate an acoustic signal and that they record an acoustic signal from a receiving transducer, measuring the transit time of the signal between the transducers. The system processes this information, yielding the sound velocity and concentration of a gas component.

Figure 4:
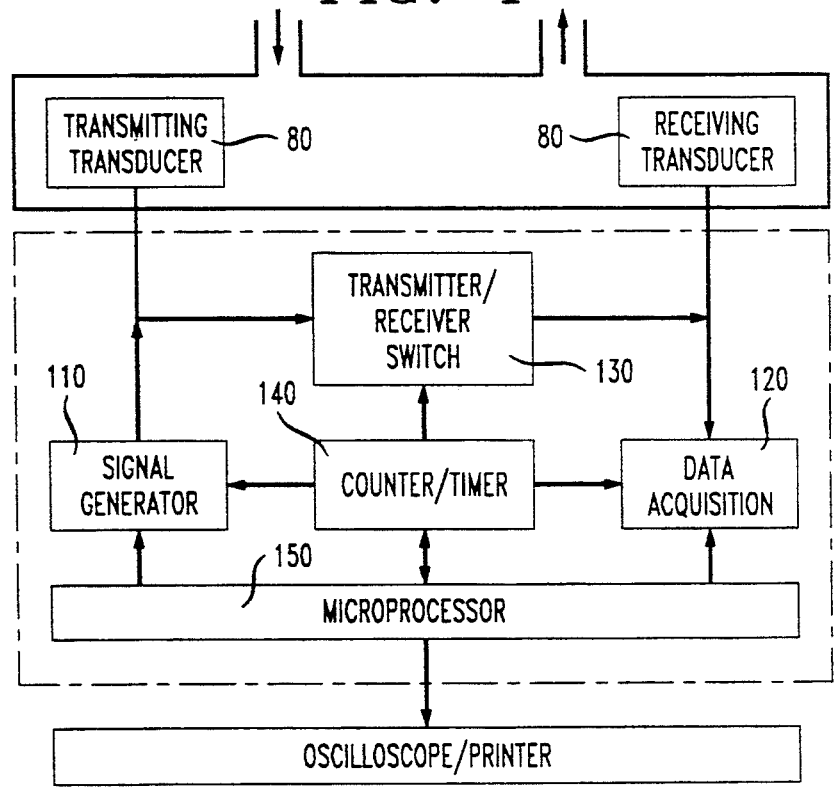
FIG. 4 is a schematic block diagram of the signal generating and data processing circuit used with the acoustic gas analysis cell of FIG. 1.

An example of a preferred signal generation/data processing system which may be employed with the acoustic cells of the invention is illustrated schematically in FIG. 4. The transducers 80 are connected to a signal generator 110, for transmission of ultrasound, and to a data acquisition device 120 for receiving ultrasound. A switch 130 alternates the connection of the transducers between signal generator 110 and data acquisition device 120, permitting each transducer to be used as either a transmitting or a receiving transducer.

Both the signal generator 110 and the data acquisition device 120 are controlled by microprocessor 150 and counter/timer 140. The microprocessor, in addition to controlling the circuit, processes the transit times of the sound waves, using the transducer separation distance to obtain the velocity. The microprocessor uses the velocity to solve the quadratic equation for the concentration of a gas mixture constituent. The microprocessor may further be connected to a feedback loop which controls the flow of the gas constituent in response to the measured concentration.

An example of a signal generator/receiver system which may be employed with the acoustic cells of the invention is Panametrics Inc. Model 5055PR. In this device, the transmitting transducer is energized by a trigger-type, pulse-forming circuit that produces short pulses. The received pulses are amplified, shaped, and then used to synchronize the original pulse-forming circuit.

A further example of a system used to generate and receive pulses which may be used with the acoustic cells of the invention is Panametrics Inc. Model 6068. This system drives the transmitter with a binary phase-encoded signal, typically 4 to 20 cycles in length. The received signal is digitized using a "flash" analog to digital (A/D) converter and determines the transit time by correlating the encoded transmitted signal with the digitized received signal. When using this system, the velocity of sound in the medium being analyzed must first be approximated before an accurate measurement can be made. This is due to the fact that a window must be centered around the receiving signal to reduce the range of sound wave measurements so that pattern recognition can be effective.

Because the velocity of sound in a gas is also dependent upon the gas temperature, for greatest accuracy it is important to conduct the sound measurements at the same temperature. To this end, the acoustic cell and gas lines can be positioned within a standard exhausted gas cabinet which provides constancy in the temperature of the system to within ±0.1° C. Alternatively, a thermocouple can be positioned within the acoustic cell and the gas temperature can be input to the microprocessor along with the transit time for determining the gas composition.

In use, the acoustic gas analysis cell 10 is coupled to a gas flow line through gas ports 70. To calibrate the system, the distance between the transducers is accurately determined using inert gases such as argon and helium. The transmitting transducer launches a pulse of sound at the resonant frequency which passes through the gas contained within conduit 20. For lead zirconate titanate (PZT) transducers, this resonant frequency is approximately 100 kHz to 250 kHz depending upon the thickness and geometry of the PZT material.

The transmitted pulse is detected by the receiving transducer which is axially aligned with the transmitting transducer. Because the transducers operate at the same frequency and are acoustically matched, either transducer 80 in the acoustic cell of FIG. 1 can be selected as the transmitting transducer, the remaining transducer being used as the receiving transducer. To improve measurement accuracy, the transducers can be operated in an alternating mode, i.e., the transducers alternately send and receive signals. Using this mode of operation, the transit time of the ultrasonic pulses is measured both with and against the direction of gas flow. The velocity is the average of the measured upstream and downstream velocities.

Using the velocity, the composition of the gas mixture is obtained. The concentration of a particular gas component is calculated by solving for x in the above quadratic equation. A list of coefficients used to solve the quadratic equation for various binary gas mixtures is given in Table 1 below:

| | List of Coefficients for Quadratic Formulation | | | | |
|---|---|---|---|---|---|
| Binary Gas | a | b | $c \times 10^{-3}$ | $d \times 10^{-3}$ | A |
| 1.) $AsH_3/H_2$ | 1.269 | 1.405 | 77.946 | 2.01594 | 2,478.909 |
| 2.) $PH_3/H_2$ | 1.289 | 1.405 | 33.9978 | 2.01594 | 2,478.909 |
| 3.) Ar/He | 1.669 | 1.630 | 39.948 | 4.0026 | 2,478.909 |
| 4.) $NH_3/H_2$ | 1.304 | 1.405 | 17.031 | 2.01594 | 2,478.909 |
| 5.) $SiH_4/H_2$ | 1.241 | 1.405 | 32.118 | 2.01594 | 2,478.909 |
| 6.) $H_2Se/H_2$ | 1.314 | 1.405 | 80.976 | 2.01594 | 2,478.909 |
| 7.) $HCl/H_2$ | 1.399 | 1.405 | 36.461 | 2.01594 | 2,478.909 |
| 8.) $N_2/H_2$ | 1.407 | 1.405 | 14.0067 | 2.01594 | 2,478.909 |
| 9.) $CH_4/H_2$ | 1.305 | 1.405 | 16.043 | 2.01594 | 2,478.909 |
| 10.) $NH_3/N_2$ | 1.307 | 1.407 | 17.031 | 14.0067 | 2,478.909 |
| 11.) $GeH_4/H_2$ | 1.227 | 1.405 | 76.63 | 2.01594 | 2,478.909 |
| 12.) $TMI/H_2$ (trimethyl indium) | 1.10 | 1.403 | 159.925 | 2.01594 | 3,102.481 |
| 13.) $TMG/H_2$ (trimethyl gallium) | 1.10 | 1.403 | 114.825 | 2.01594 | 3,102.481 |

The acoustic cells and methods described herein find application in various chemical vapor deposition processes. Deposition of glasses for fiber optic preform fabrication is an example of such a chemical vapor deposition process. Mixtures of silicon tetrachloride, $SiCl_4$, with oxygen and mixtures of germanium tetrachloride, $GeCl_4$, with oxygen are used to build up glass layers on the inside wall of a rotating silica tube to produce a graded index profile. For multimode fibers, the deposited layers become the core and the silica tube becomes the cladding. Further process parameters can be found in MacChesney et al., Proc. IEEE, Vol. 62 (1974), p. 1280, the disclosure of which is incorporated by reference herein. The acoustic cells are used to control the relative proportions of $SiCl_4$ and oxygen and $GeCl_4$ and oxygen.

The acoustic cells and methods of the present invention can be used individually for measurement of binary gas mixtures, or in series and parallel combinations for measurement of gas mixtures having more than two constituents. For example, an acoustic cell may be placed in a gas line to measure a first binary gas mixture. This binary mixture may then be further mixed with a third gas and a second acoustic cell may be used to control the relative proportions of the binary gas mixture and the third gas. The third gas may be a single gas or may itself be a binary gas mixture, the relative concentrations of its components having been controlled by an acoustic cell upstream of the later mixing point.

While the foregoing invention has been described with respect to the preferred embodiments, it is understood that various changes and modifications such as those suggested above, but not limited thereto, may be made without departing from the scope of the claims.

We claim:

1. An acoustic cell for determining the composition of a gas mixture comprising:
    a hollow conduit for containing a gas mixture to be analyzed, said conduit having first and second ends;
    a first transducer housing sealingly engaged with said first end of the conduit, said first transducer housing supporting a first transducer, and having an acoustic isolation material positioned at least partially between said first transducer and said first transducer housing to acoustically isolate said first transducer from said first transducer housing;
    a second transducer housing sealingly engaged with said second end of the conduit, said second transducer housing supporting a second transducer and having an acoustic isolation material positioned at least partially between said second transducer and said second transducer housing to acoustically isolate said second transducer from said second transducer housing,
    a first gas port coupled to said first end of the conduit; and
    a second gas port coupled to said second end of the conduit;
    wherein said acoustic isolation of said first transducer from said first transducer housing and said acoustic isolation of said second transducer from said second transducer housing produces a signal-to-noise ratio of at least 4 to 1.

2. An acoustic cell as recited in claim 1 wherein said first and second transducers are acoustically matched.

3. An acoustic cell as recited in claim 1 wherein said first and second transducers resonate at a frequency between 50 and 300 kilohertz.

4. An acoustic cell as recited in claim 1 wherein said acoustic isolation material is an elastomer.

5. An acoustic cell as recited in claim 4 wherein said acoustic isolation material is a silicone elastomer.

6. An acoustic cell as recited in claim 1 further comprising impedance matching material positioned between said first transducer and said first end of said conduit and impedance matching material positioned between said second transducer and said second end of said conduit.

7. An acoustic cell as recited in claim 6 wherein said impedance matching material is an elastomer.

8. An acoustic cell as recited in claim 7 wherein said impedance matching material is a silicone elastomer.

* * * * *